United States Patent [19] [11] Patent Number: 4,944,308
Åkerfeldt [45] Date of Patent: Jul. 31, 1990

[54] TISSUE SAMPLING DEVICE

[75] Inventor: Dan Åkerfeldt, Uppsala, Sweden

[73] Assignee: C. R. Bard, Inc., Murray Hill, N.J.

[21] Appl. No.: 270,368

[22] Filed: Nov. 14, 1988

[30] Foreign Application Priority Data

Nov. 19, 1987 [SE] Sweden ................................ 8704559

[51] Int. Cl.⁵ ............................................. A61B 10/00
[52] U.S. Cl. ...................................... 128/751; 128/754
[58] Field of Search ............... 128/749, 751, 753, 754,
128/757, 305, 310; 604/21, 22, 51, 160, 164,
165, 166, 264

[56] References Cited

U.S. PATENT DOCUMENTS

| 4,308,875 | 1/1982 | Young | 128/753 |
| 4,600,014 | 7/1986 | Beraha | 128/754 |
| 4,699,154 | 10/1987 | Lindgren | 128/754 |
| 4,702,261 | 10/1987 | Cornell et al. | 128/754 |
| 4,735,215 | 4/1988 | Goto et al. | 128/754 |
| 4,766,907 | 8/1988 | de Groot et al. | 128/754 |
| 4,776,346 | 10/1988 | Beraha et al. | 128/754 |

FOREIGN PATENT DOCUMENTS

SE83/00112  3/1983  World Int. Prop. O. .

Primary Examiner—Randall L. Green
Assistant Examiner—Randy Shay
Attorney, Agent, or Firm—Jones, Askew & Lunsford

[57] ABSTRACT

The present invention briefly refers to a driving unit (1) for a device for tissue-sampling. The device comprises in addition to the driving unit a needle unit comprising a hollow outer needle (7a) and slidably disposed therein an inner needle (7b), the driving unit (1) being used to propel the needles (7a, 7b). The driving unit comprises a driving device for each needle and each driving device in turn comprises a spring mechanism adapted to be pre-tensioned. The driving unit in addition comprises an inner guide sleeve (3) containing two successive needle holders (4a, 4b) adapted to be shifted in relation to each other in the longitudinal direction of the sleeve and adapted to be pre-tensioned in the same direction for propelling the needles (7a, 7b) with the aid of one spring (5a, 5b) each and which are provided with releasable locking means (33a, 33b). A manual triggering device (6) is provided for releasing the one needle holder (4b) which in turn is adapted during the final phase of its propulsion to release the other needle holder (4a). A tensioning sleeve (2) which rotatably surrounds the guide sleeve (3) is provided with cam surfaces cooperating with the needle holders (4a, 4b) to pretension them against the spring force.

16 Claims, 3 Drawing Sheets

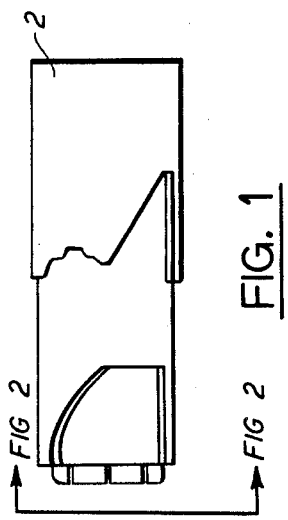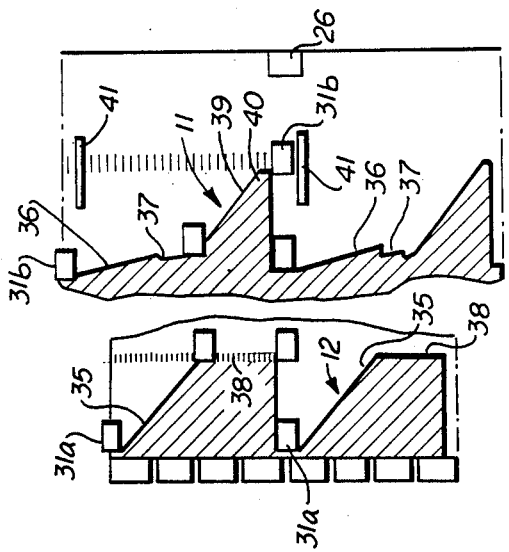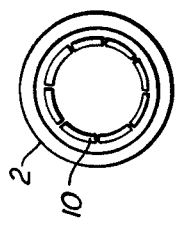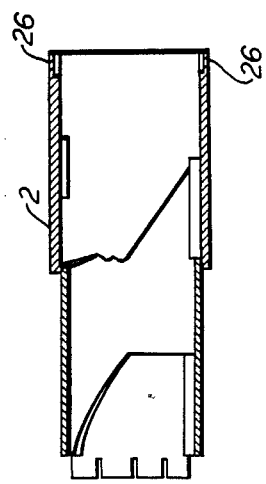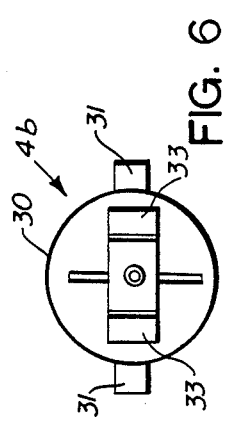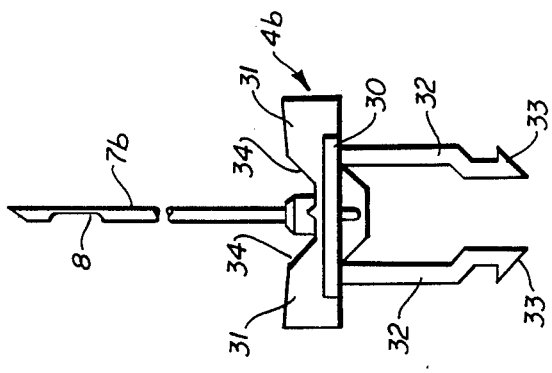

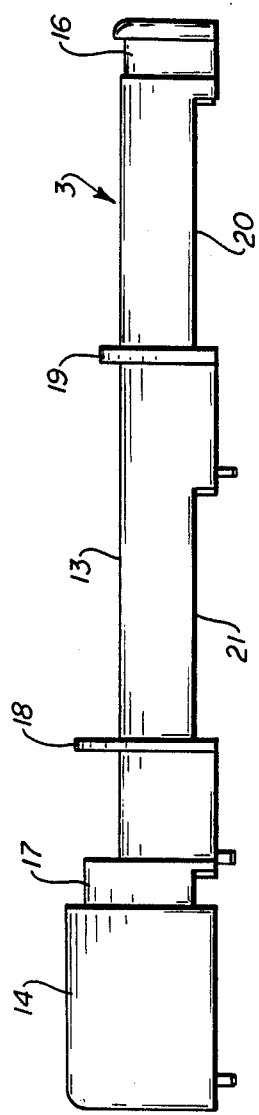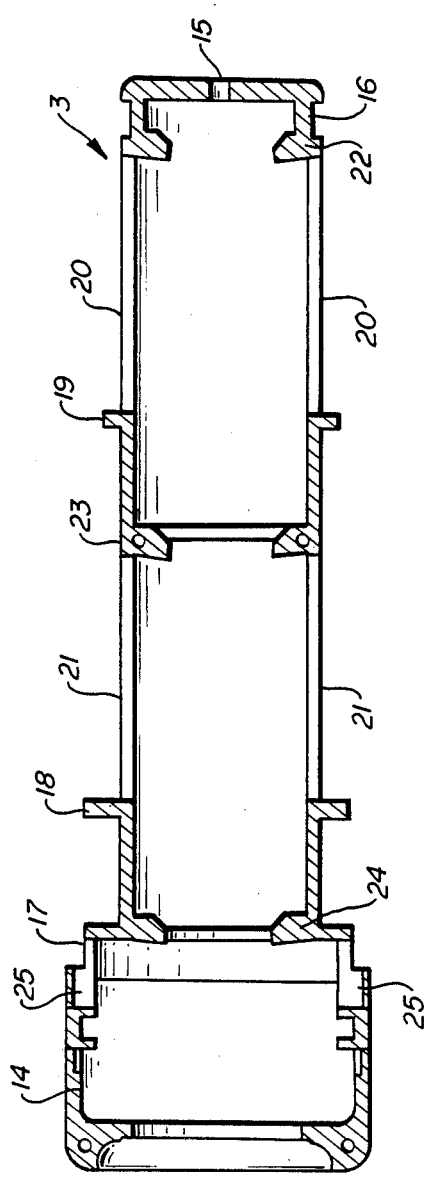

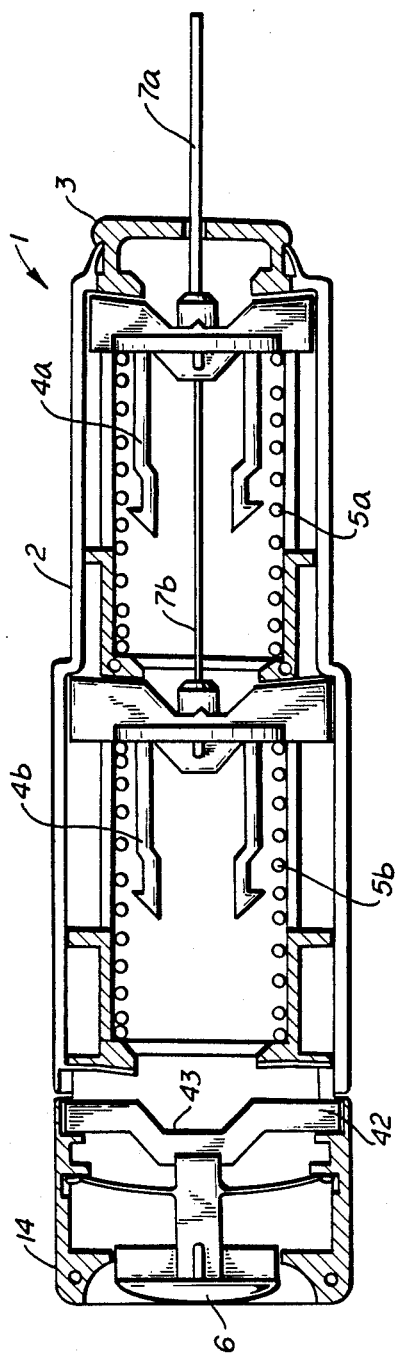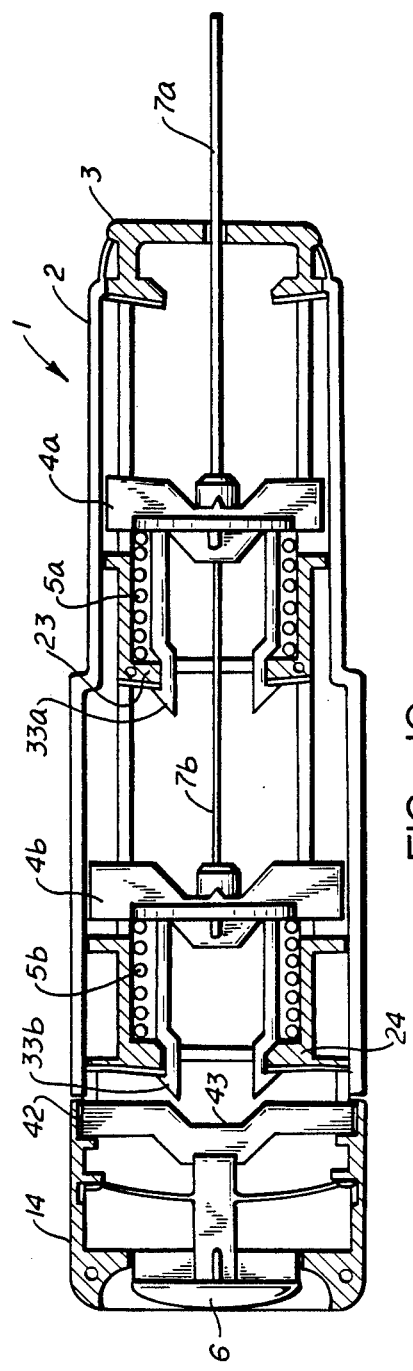

TISSUE SAMPLING DEVICE

TECHNICAL FIELD

The present invention relates to devices for tissue sampling by so-called coarse-needle puncture in which a driving unit is used to drive the needle unit used for such a sampling. Specifically the invention refers to a novel driving unit for such a sampling device.

BACKGROUND OF THE INVENTION

Recently, it has become more common to take samples of inner tissue of man and animals, so-called biopsy, in order to diagnose various diseases such as cancer. The reasons for this development include, on the one hand, that it is a reliable diagnosing method and, on the other hand, that sampling devices have been developed which are easy to use even for physicians who are not specialized in this sampling field.

A prior-art sampling device of this type is described in the Swedish patent application No. 8600755-6, which corresponds to U.S. patent application Ser. No. 890,543, now U.S. Pat. No. 4,699,154, where also the sampling procedure proper is described. The driving unit therein described is intended to be used to drive a needle unit and comprises a pair of springs which together with various guiding, locking, and triggering mechanisms are enclosed in a little box which also forms the handle of the sampling device. All the details in the box proper are made of corosion-free material of high quality, for example stainless steel. This box with its contents is impractical for the reason that it is complicated and heavy, the latter factor causing the physician to become tired when carrying the instrument. Due to the fact that the device is complicated and contains comparatively expensive material, the whole construction becomes expensive. This driving unit, however, may be sterilized and reused practically indefinitely.

However, there has been a demand for a sampling device of the above-indicated type that would be so inexpensive and simple as to be considered a single-use device, even if it is capable of being used multiple times prior to being discarded. Such a device, even though primarily intended for only a single use, could be used more than once when several samples are to be retrieved from the same patient. Moreover, there is a need for a sampling device which is lightweight so as not to fatigue the user, which has an ergonomically comfortable shape, and which permits easy tensioning of the springs of the driving unit.

SUMMARY OF THE INVENTION

Stated generally, the present invention comprises a tissue sampling device for retrieving a tissue specimen from a patient. The tissue sampling device is intended primarily as a single-use device. A hollow first needle is positioned within a guide sleeve and extends from an opening in the front wall of the guide sleeve. A second needle extends through the hollow first needle and has a tip which is extendable from the hollow first needle and the opening. The second needle further includes a tissue sample receiving recess adjacent its tip.

A first needle head is coupled to the hollow first needle and is mounted within the guide sleeve for movement along the longitudinal axis of the guide sleeve to move the hollow first needle along the axis. Similarly, a second needle head is coupled to the second needle and mounted within the guide sleeve for movement along the longitudinal axis of the guide sleeve to move the second needle along the axis. A first spring disposed within the guide sleeve and in contact with the second needle head is operative from an energized mode to propel the second needle head along the axis towards the opening, causing the tip of the second needle to be extended from the hollow first needle to expose the tissue sample receiving recess. A second spring positioned within the housing in contact with the first needle head is similarly operative from an energized mode to propel the first needle head along the axis towards the opening, thus causing the hollow first needle to be extended from the opening so that the recess of the second needle is enclosed by the hollow first needle.

A tensioning sleeve is rotatably mounted on the guide sleeve and is operative upon rotation thereof to move the needle heads along the longitudinal axis of the guide sleeve towards the back of the guide sleeve to energize the springs. In the disclosed embodiment of the invention, the tensioning sleeve is operative to energize the springs sequentially, rather than concurrently, thereby reducing the amount of force which must be exerted to energize the device. When the springs have been energized, a first latch releasable from outside the guide sleeve releasably holds the first spring in the energized mode, and a second latch releasably holds the second spring in the energized mode and is releasable in response to and subsequent to release of the first spring.

When it is desired to retrieve a tissue sample, the device is energized, the tip of the needle assembly is placed adjacent the tissue to be sampled, and the first latch is released. The first spring propels the second needle head along the longitudinal axis of the guide sleeve and towards the opening, causing the tip of the second needle to be extended from the hollow first needle and into the tissue such that a tissue sample is captured within the tissue sample receiving recess. In response to and subsequent to release of the first spring, the second latch is released, whereupon the second spring propels the first needle head along the longitudinal axis of the guide sleeve and towards the opening. The hollow first needle is thus extended from the opening to enclose the sample receiving recess of the second needle, thereby trapping the sample between the needles so as to permit it to be removed from the patient.

Thus, it is the purpose of the present invention to eliminate the drawbacks inherent in prior-art driving units and to fulfill the above-mentioned needs and requirements. This purpose is achieved by means of a driving unit of the type indicated in the claims, from which the specific characteristic features of the invention also will appear.

BRIEF DESCRIPTION OF THE DRAWINGS

FIG. 1 is a side view of a sleeve forming the outer wall of the driving unit,

FIG. 2 is an end view of the sleeve shown in FIG. 1 seen in the direction of the arrows II—II, FIG. 3 is a central longitudinal section of the sleeve shown in FIGS. 1 and 2, FIG. 4 is a flattened view of the sleeve shown in FIGS. 1 to 3, FIG. 5 is a side view of the needle holder of the solid needle, it being understood that the needle holder for the tubular needle has a substantially corresponding shape, FIG. 6 is an end view of the end opposite to the needle of the needle holder shown in FIG. 5, FIG. 7 is a side view of one half of the guide sleeve composed of two halves, FIG. 8 is a plan view from the concave side of the sleeve half shown in FIG. 7, FIG. 9 is a section of the driving unit according to the invention in the released condition, and FIG. 10 is a section corresponding to FIG. 9 but showing the portions in their pre-tensioned condition.

DETAILED DESCRIPTION OF THE DISCLOSED EMBODIMENT

A sampling device for biopsy purposes consists in this case of a needle unit and a driving unit combined in one unit. As mentioned initially, the needle unit and the sampling procedure are previously known and will therefore not be described in detail.

The driving unit 1 comprises an outer tensioning sleeve 2 (FIGS. 1 to 4), an internal guide sleeve 3 (FIGS. 7 and 8), two needle holders 4 (FIGS. 5 and 6), two driving springs 5 and a triggering knob 6 (FIGS. 9 and 10). Attached within the one needle holder 4a is a tubular needle 7a whereas attached to the other needle holder 4b is a solid needle 7b having a cavity 8 (FIG. 5) for receiving a tissue sample, said latter needle 7b extending slidably through the tubular needle 7a.

In FIG. 1 there is shown the outer sleeve or tensioning sleeve 2 forming the outer wall of the driving unit. As appears from FIG. 2, this sleeve is of substantially circular cross-section but has step-wise diminishing diameter. At its narrow end it carries a set of tongues 10, the free outer ends of which are radially pre-tensioned in an inward direction. The function of these tongues will be described later. The steps between the various diameters form cam surfaces, a rear cam surface 11 and a forward cam surface 12 extending radially into the sleeve. In the embodiment shown these cam surfaces 11, 12 are double which means that the cam surfaces 11, 12 are symmetrically repeated twice on the circumference. The shape and function of the cam surfaces 11, 12 will be described hereinbelow.

The inner sleeve or guide sleeve 3 comprises two identical halves 13 which may be put together in a conventional way with the aid of pins and holes to form a unit of substantially cylindrical shape and circular cross section. At one end the guide sleeve 3 has a handle 14 and at the other end an axially directed hole 15 through which the needles 7a, 7b are to extend and which also forms a guide for these needles, and at the same end a radially inwardly extending circular groove 16 adapted to receive the tongues 10 of the tensioning sleeve 2. On the handle 14 a circular depression 17 is provided facing in an inward direction and adapted to be inserted into the tensioning sleeve 2 when the unit is assembled. The guide sleeve also has two circular flanges 18, 19 adapted to abut against the inner surface of the tensioning sleeve 2, and two pairs of axially extending guide grooves 20, 21 in diametrically opposed positions and extending through the wall of the guide sleeve 3.

Within the guide sleeve 3 there are provided a circular shoulder 22 at the needle end forming an abutment for the forward needle holder 4a, an intermediate circular shoulder 23 forming, on the one hand, an abutment for the rear needle holder 4b and, on the other hand, a seat for the driving spring 5a for the forward needle holder 4a, and a rear circular shoulder 24 forming a seat for the driving spring 5b for the rear needle holder 4b.

Both the rear shoulder 24 and the intermediate shoulder 23 also form parts of the locking mechanism during loading or tensioning of the driving unit of the sampling device, in particular if the driving springs 5a and 5b are compressed.

Within the handle 14 there are in addition provided two opposite axially extending grooves 25 coacting with grooves or recesses 26 in the tensioning sleeve 2 to prevent the sampling device from being triggered except in one definite position, as well as guides for the triggering knob 6.

As appears from FIGS. 5 and 6, the needle holders 4 comprise a circular plate 30 having a slightly reduced diameter in comparison with the inner diameter of the guide sleeve 3. On the one side of plate 30 a pair of radially extending wings 31 are provided extending slightly beyond the periphery of plate 30. On the opposite side of the plate 30 a pair of axially extending arms 32 are provided, said arms being resilient and provided at the outer free ends with outwardly extending hooks 33. These hooks 33 are adapted in the tensioned condition to rest behind a shoulder 23 and 24 respectively, a pressure spring 5a, 5b being inserted about the arms 32 between the plate 30 and the respective shoulder 23, 24. Each of the wings 31 has a downwardly and inwardly sloping surface 34. For releasing the sampling device, these surfaces 34 cooperate with the hooks 33 of the arms 32, the hooks 33 sliding along the surfaces 34 and being shifted towards each other to release them from their engagement with the respective shoulder 23, 24.

The wings 31 are guided in slots 20, 21 thus preventing a rotation of the needle holders 4 in relation to the guide sleeve 3. The wings 31 extend through slots 20, 21 towards the inner surface of the tensioning sleeve 2, however, suitably not into contact therewith in a radial direction but into abutment with the cam surfaces 11, 12 therein.

The assemblage of the driving unit 1 is performed substantially in the following way: The two needle holders 4a, 4b together with their needles 7a, 7b and with the springs 5a, 5b positioned about arms 32 are placed in position in the one half of the guide sleeve 3 and also the trigger knob 6 is inserted therein, whereafter the other half of the guide sleeve 3 is placed on the first half. Thereafter, the tensioning sleeve 2 is passed over the guide sleeve 3 causing the tongues 10 to enter into groove 16, while the opposite end of the tensioning sleeve 2 encloses the guide sleeve 3 at the depression 17. In this position the unit is ready for use. It will be appreciated that the parts used are of simple and cheap construction, to the extent possible consisting of plastics or similar material, only springs 5a, 5b and the needles 7a, 7b proper consisting of metal and in addition being light-weight.

The driving unit of the sampling device operates as follows: The sampling device, which in itself is of the single-use type, may be loaded several times without problems and is manufactured with different needle thicknesses and needle lengths depending on the specific use. The physician thus chooses a sampling device adapted for the sampling in question. This device, however, is not initially tensioned in order to avoid deformation of certain parts due to the spring forces, but tensioning is to be performed immediately prior to sampling. For this purpose the handle 14 is held with the one hand while the other hand seizes the tensioning sleeve 2 to perform relative rotation of these parts. The wings 31a of the forward needle holder 4a thereby will be shifted along the steep portion of the cam surface 12 thereby compressing the forward spring 5a. The wings 31b of the rear needle holder 4b follow at the same time the flattened portion 36 of the cam surface 11 to arrive at the end behind catch 37. In this position backward rotation to the starting position is no longer possible, but the rear needle holder 4b is raised to such an extent that it cannot come into contact with the hooks 33a of the forward needle holder 4a when these enter into the locking position behind the intermediate shoulder 23. During continued rotation the forward wings 31a follow the plane cam surface 38a whereas the rear wings 31b follow the steep cam surface 39 causing the rear spring 5b to be compressed. If the physician should lose his grip during this part of the tensioning procedure, the rear needle holder 4b moves towards the starting position but is retained in front of catch 37 and thus cannot release the forward needle holder 4a.

When wings 31b have been advanced along cam surface 39 during continued rotation, they are lifted over a catch 40. Thereafter reverse rotation is impossible and continued rotation is prevented by an abutment 41. In this position the recesses 26 are situated exactly opposite grooves 25 in the guide sleeve 3 and the triggering knob 6 may be depressed. The sampling device is now tensioned and ready for sampling.

The triggering knob 6 is connected to a cross element 42 having a substantially V-shaped depression 43 in its central portion. When the triggering knob 6 is depressed, which is possible due to the fact that grooves 25 and 26 are mutually aligned, the flanges of the V-shaped portion 43 will urge hooks 33b towards each other causing them to loose contact with shoulder 24 and enabling the spring 5b to propel the inner needle 7b. When the needle holder 4b approaches shoulder 23 it performs the same function as previously performed by the triggering knob and releases the forward needle holder 4a from its engagement with the intermediate shoulder 23. Consequently, the inner needle 7b having a tissue-receiving cavity 8, is propelled first whereafter the tubular outer needle is released to resect the tissue received in said cavity. If additional samples are to be taken, the first needle 7a is to be withdrawn, which means that the sleeve 2 is to be rotated in relation to handle 14 to the first locking position in which the wings 31b are retained behind catch 37.

In the embodiment shown the wings 31 of the needle holders 4a, 4b extend in both directions, which means that they cooperate with one cam surface each. Due to this, these cam surfaces must be relatively steep because both springs are to be tensioned during half rotation of the tensioning sleeve 2 in relation to the guide sleeve 3. By providing the needle holders with only one wing adapted to cooperate with cam surfaces in the tensioning sleeve 2, these cam surfaces may be flattened, as the tensioning of both springs in this case may be performed during a full-turn rotation.

In the embodiment shown the needles 7a, 7b are so positioned as to extend centrally from the driving unit 1. If the sampling is to be performed with the aid of additional apparatus means, e.g. an ultrasonic apparatus in order to determine the penetration of the needle unit, such a positioning of the needle may be less suitable. Accordingly, other positions of the needles, e.g. eccentric positioning, are within the scope of the invention.

The sequential tensioning sequence hereinabove described, wherein rotation of the tensioning sleeve energizes first one spring and then the other, provides several advantages over prior art tissue sampling devices. First, since only one spring at a time is being energized, the physician need exert only enough force on the tensioning sleeve to overcome the force of one spring, rather than having to overcome the force of both springs simultaneously. Further, since initial rotation of the tensioning sleeve biases the first needle head rearward but not the second needle head, partial rotation of the tensioning sleeve will retract the hollow outer needle but leave the inner needle extended. Thus, after retrieving a tissue sample, the physician can partially rotate the tensioning sleeve to expose the tissue sample receiving recess, thereby providing access to the retrieved specimen. In contrast, prior art sampling devices have heretofore required disassembly of the device and removal of the needles from the driving unit to retrieve the tissue sample.

The expert in this field will realize that the driving unit according to this invention fully achieves the initially defined purpose. The expert also will realize many possible variations and modifications of the invention. However, such variations and modifications are intended to fall within the scope of the invention as defined in the attached claims.

I claim:
1. A tissue sampling device comprising:
   a housing having front and rear housing ends and defining a longitudinal axis extending between said front and rear housing ends, and said front housing end having an opening therethrough;
   a hollow first needle positioned within said housing and extendable from said opening, said hollow first needle being moveable along said axis;
   a second needle extending through said hollow first needle and movable along said axis, said second needle having a tip which is extendable from said hollow first needle and said opening, and said second needle further including a tissue sample receiving recess;
   a first needle head coupled to said hollow first needle and mounted within said housing for movement along said axis to move said hollow first needle along said axis;
   a second needle head coupled to said second needle and mounted within said housing for movement along said axis to move said second needle along said axis;
   a first spring disposed within said housing and bearing directly against said second needle head, said first spring being capable of being placed into an energized mode to store energy, and said first spring being releasable from said energized mode to propel said second needle head along said axis towards said opening, such that said tip of said second needle is extended from said hollow first needle, whereby a tissue sample can be captured within said recess;
   a second spring positioned within said housing and bearing directly against said first needle head, said second spring being capable of being placed into an energized mode to store energy, and said second spring being releasable from said energized mode to propel said first needle head along said axis towards said opening, said hollow first needle being extended from said opening such that said recess of said second needle is enclosed by said hollow first needle;

a first latch means selectively releasable from outside said housing for releasably holding said first spring in said energized mode; and a second latch means for releasably holding said second spring in said energized mode, said second latch means being releasable in response to and subsequent to release of said first spring.

2. A tissue sampling device comprising:

a housing having front and rear housing ends and defining a longitudinal axis extending between said front and rear housing ends, said housing having an exterior surface, said housing having longitudinal slot means formed therein, and said front housing end having an opening therethrough;

a hollow first needle positioned within said housing and extendable from said opening, said hollow first needle being moveable along said axis;

a second needle extending through said hollow first needle and movable along said axis, said second needle having a tip which is extendable from said hollow first needle and said opening, and said second needle further including a tissue sample receiving recess;

a first needle head coupled to said hollow first needle and mounted within said housing for movement along said axis to move said hollow first needle along said axis, said first needle head having a portion thereof extending through said longitudinal slot means so as to be engageable from outside said housing;

a second needle head coupled to said second needle and mounted within said housing for movement along said axis to move said second needle along said axis, said second needle head having a portion thereof extending through said longitudinal slot means so as to be engageable from outside said housing;

a first spring disposed within said housing and in contact with said second needle head, said first spring being capable of being placed into an energized mode to store energy by biasing said second needle head along said axis away from said opening, and said first spring being releasable from said energized mode to propel said second needle head along said axis towards said opening, such that said pointed end of said second needle is extended from said hollow first needle, whereby a tissue sample can be captured within said recess;

a second spring positioned within said housing in contact with said first needle head, said second spring being capable of being placed into an energized mode to store energy by biasing said first needle head along said axis away from said opening, said first needle thereby being retracted through said opening, and said second spring being releasable from said energized mode to propel said first needle head along said axis towards said opening, said hollow first needle being extended from said opening such that said recess of said second needle is enclosed by said hollow first needle;

said second spring being capable of being placed into said energized mode independently of said first spring being placed in said energized mode, whereby said hollow first needle but not said second needle is retracted through said opening such that said recess in said second needle is exposed;

a first latch means selectively releasable from outside said housing for releasably holding said first spring in said energized mode; and a second latch means for releasably holding said second spring in said energized mode, said second latch means being releasable in response to and subsequent to release of said first spring.

3. The tissue sampling device of claim 2, further comprising energizing means movably mounted to said housing and operative to engage said portions of said first and second needle heads extending through said longitudinal slot means for biasing said first and second needle heads along said axis away from said opening to place said second and first springs into said energized modes, said energizing means being selectively operable to place said second spring into said energized mode independently of said first spring being placed in said energized mode.

4. A tissue sampling device comprising:

a housing having front and rear housing ends and defining a longitudinal axis extending between said front and rear housing ends, said housing having an exterior surface, said housing having longitudinal slot means formed therein, and said front housing end having an opening therethrough;

a hollow first needle positioned within said housing and extendable from said opening, said hollow first needle being moveable along said axis;

a second needle extending through said hollow first needle and movable along said axis, said second needle having a tip which is extendable from said hollow first needle and said opening, and said second needle further including a tissue sample receiving recess;

a first needle head coupled to said hollow first needle and mounted within said housing for movement along said axis to move said hollow first needle along said axis;

a second needle head coupled to said second needle and mounted within said housing for movement along said axis to move said second needle along said axis;

a first spring disposed within said housing and in contact with said second needle head, said first spring being capable of being placed into an energized mode to store energy by biasing said second needle head along said axis away from said opening, and said first spring being releasable from said energized mode to propel said second needle head along said axis towards said opening, such that said pointed end of said second needle is extended from said hollow first needle, whereby a tissue sample can be captured within said recess;

a second spring positioned within said housing in contact with said first needle head, said second spring being capable of being placed into an energized mode to store energy by biasing said first needle head along said axis away from said opening, said first needle thereby being retracted through said opening, and said second spring being releasable from said energized mode to propel said first needle head along said axis towards said opening, said hollow first needle being extended from said opening such that said recess of said second needle is enclosed by said hollow first needle;

energizing means movably mounted to said housing and operative to engage said first and second needle heads through said longitudinal slot means, said energizing means being capable of placing said second spring into said energized mode independently of said first spring being placed in said energized mode, whereby said hollow first needle but not said second needle is retracted through said opening such that said recess in said second needle is exposed;

a first latch means selectively releasable from outside said housing for releasably holding said first spring in said energized mode; and a second latch means for releasably holding said second spring in said energized mode, said second latch means being releasable in response to and subsequent to release of said first spring.

5. A tissue sampling device comprising:

a guide sleeve having front and rear guide sleeve ends and defining a longitudinal axis extending between said front and rear guide sleeve ends, said front guide sleeve end having an opening therethrough;

a hollow first needle positioned within said guide sleeve and extendable from said opening, said hollow first needle being moveable along said axis;

a second needle extending through said hollow first needle and movable along said axis, said second needle having a tip which is extendable from said hollow first needle and said opening, and said second needle further including a tissue sample receiving recess;

a first needle head coupled to said hollow first needle and mounted within said guide sleeve for movement along said axis to move said hollow first needle along said axis;

a second needle head coupled to said second needle and mounted within said guide sleeve for movement along said axis to move said second needle along said axis;

a first spring disposed within said guide sleeve and operatively associated with said second needle head, said first spring being capable of being placed into an energized mode to store energy, and said first spring being releasable from said energized mode to propel said second needle head along said axis towards said opening, such that said tip of said second needle is extended from said hollow first needle, whereby a tissue sample can be captured within said recess;

a second spring positioned within said guide sleeve and operatively associated with said first needle head, said second spring being capable of being placed into an energized mode to store energy, and said second spring being releasable from said energized mode to propel said first needle head along said axis towards said opening, said hollow first needle being extended from said opening such that said recess of said second needle is enclosed by said hollow first needle;

a first latch means selectively releasable from outside said guide sleeve for releasably holding said first spring in said energized mode;

a second latch means for releasably holding said second spring in said energized mode, said second latch means being releasable in response to and subsequent to release of said first spring; and a tensioning sleeve rotatably mounted on said guide sleeve and operative upon rotation thereof to move said first needle head and said second needle head along said axis towards said rear guide sleeve end to cause said first latch means to hold said first spring in said energized mode and to cause said second latch means to hold said second spring in said energized mode.

6. The tissue sampling device of claim 5, wherein said tensioning sleeve includes means for moving said first and second needle heads sequentially, whereby said first and second springs are energized consecutively.

7. The tissue sampling device of claim 5, wherein said tensioning sleeve includes means for selectively moving said first needle head but not said second needle head towards said rear guide sleeve end, whereby said hollow first needle is selectively retractable to expose said tissue sample receiving recess in said second needle.

8. The tissue sampling device of claim 5, wherein said tensioning sleeve further comprises first and second cam surfaces, said first cam surface engaging said first needle head and said second cam surface engaging said second needle head as said tensioning sleeve is rotated to bias said first and second needle heads along said axis towards said rear guide sleeve end.

9. The tissue sampling device of claim 8, wherein said first and second cam surfaces are configured such that said first cam surface engages said first needle head as said tensioning sleeve is first rotated to bias said first needle head along said axis towards said rear guide sleeve end, and subsequently said second cam surface engages said second needle head as said tensioning sleeve is further rotated to bias said second needle head along said axis towards said rear guide sleeve end.

10. The tissue sampling device of claim 5, further comprising means for preventing rotation of said first and second needles.

11. The tissue sampling device of claim 10, wherein said means for preventing rotation of said first and second needles comprises:

means defining longitudinal slots in said guide sleeve; and wings formed on said first and second needle heads for engaging said longitudinal slots in said guide sleeve.

12. The tissue sampling device of claim 11, wherein a portion of each of said wings on said first and second needle heads projects through said longitudinal slots and exteriorly of said guide sleeve, and wherein said tensioning sleeve further comprises first and second cam surfaces, said first cam surface engaging said projecting portion of said wing formed on said first needle head, and said second cam surface engaging said projecting portion of said wing formed on said second needle heads such that rotation of said tensioning sleeve causes said cam surfaces to bias said first and second needle heads along said axis towards said rear guide sleeve end.

13. The tissue sampling device of claim 5, wherein said guide sleeve further comprises first and second shoulders disposed within said guide sleeve, wherein said first latch comprises a resilient tab formed on said second needle head for engaging said first shoulder for releasably holding said first spring in said energized mode, and wherein said second latch comprises a resilient tab formed on said first needle head for engaging said second shoulder for releasably holding said second spring in said energized mode.

14. The tissue sampling device of claim 13, wherein said second needle head further comprises a wedge surface configured such that when said first spring urges said second needle head along said axis towards said opening, said wedge surface engages said resilient tab formed on said first needle head to bias said tab out of engagement with said second shoulder, thereby to release said first needle head for travel along said axis towards said opening.

15. A tissue sampling device comprising:
a guide sleeve having front and rear guide sleeve ends and defining a longitudinal axis extending between said front and rear guide sleeve ends, said front guide sleeve end having an opening therethrough;
a hollow first needle positioned within said guide sleeve and extendable from said opening, said hollow first needle being moveable along said axis;
a second needle extending through said hollow first needle and moveable along said axis, said second needle having a tip which is extendable from said hollow first needle and said opening, and said second needle further including a tissue sample receiving recess;
a first needle head coupled to said hollow first needle and mounted within said guide sleeve for movement along said axis to move said hollowing first needle along said axis;
a second needle head coupled to said second needle and mounted within said guide sleeve for movement along said axis to move said second needle along said axis;
a first spring disposed within said guide sleeve and operatively associated with said second needle head, said first spring being capable of being placed into an energized mode to store energy, and said first spring being releasable from said energized mode to propel said second needle head along said axis towards said opening, such that said tip of said second needle is extended from said hollow first needle, whereby a tissue sample can be captured within said recess;
a second spring positioned within said guide sleeve and operatively associated with said first needle head, said second spring being capable of being placed into an energized mode to store energy, and said second spring being releasable from said energized mode to propel said first needle head along said axis towards said opening, said hollow first needle being extended from said opening such that said recess of said second needle is enclosed by said hollow first needle;
a first latch means selectively releasable from outside said guide sleeve for releasably holding said first spring in said energized mode;
a second latch means for releasably holding said second spring in said energized mode, said second latch means being releasable in response to and subsequent to release of said first spring; and
sequential energizing means operative to move said first needle head along said axis towards said rear guide sleeve end to cause said second latch means to hold said second spring in said energized mode, and subsequently to move said second needle head along said axis towards said rear guide sleeve end to cause said first latch means to hold said first spring in said energized mode.

16. A tissue sampling device comprising:
a guide sleeve having front and rear guide sleeve ends and defining a longitudinal axis extending between said front and rear guide sleeve ends, said front guide sleeve end having an opening therethrough;
a hollow first needle positioned within said guide sleeve and extendable from said opening, said hollow first needle being movable along said axis;
a second needle extending through said hollow first needle and moveable along said axis, said second needle having a tip which is extendable from said hollow first needle and said opening, and said second needle further including a tissue sample receiving recess;
a first needle head coupled to said hollow first needle and mounted within said guide sleeve for movement along said axis to move said hollow first needle along said axis;
a second needle head coupled to said second needle and mounted within said guide sleeve for movement along said axis to move said second needle along said axis;
a first spring disposed within said guide sleeve and operatively associated with said second needle head, said first spring being capable of being placed into an energized mode to store energy, and said first spring being releasable from said energized mode to propel said second needle head along said axis towards said opening, such that said tip of said second needle is extended from said hollow first needle, whereby a tissue sample can be captured within said recess;
a second spring positioned within said guide sleeve and operatively associated with said first needle head, said second spring being capable of being placed into an energized mode to store energy, and said second spring being releasable from said energized mode to propel said first needle head along said axis towards said opening, said hollow first needle being extended from said opening such that said recess of said second needle is enclosed by said hollow first needle;
a first latch means selectively releasable from outside said guide sleeve for releasably holding said first spring in said energized mode;
a second latch means for releasably holding said second spring in said energized mode, said second latch means being releasable in response to and subsequent to release of said first spring; and
energizing means operative to move said first needle head and said second needle head along said axis towards said rear guide sleeve end to cause said first latch means to hold said first spring in said energized mode and to cause said second latch means to hold said second spring in said energized mode, said energizing means being selectively operative to move said first needle head but not said second needle head towards said rear guide sleeve end, whereby said hollow first needle is selectively retractable to expose said tissue sample receiving means in said second needle.

* * * * *